US00PP17232P2

(12) United States Plant Patent
Leue

(10) Patent No.: US PP17,232 P2
(45) Date of Patent: Nov. 21, 2006

(54) ***ANGELONIA* PLANT NAMED 'BALANGPLUM'**

(50) Latin Name: *Angelonia angustifolia*
Varietal Denomination: Balangplum

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/269,990

(22) Filed: Nov. 9, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/2332 filed Nov. 16, 2005.

*Primary Examiner*—Kent Bell
*Assistant Examiner*—Louanne Krawczewicz Myers
(74) *Attorney, Agent, or Firm*—Audrey Charles

(57) ABSTRACT

A new and distinct cultivar of *Angelonia* plant named 'Balangplum' characterized by its medium violet-colored flowers, good basal branching and moderately vigorous, upright growth habit.

1 Drawing Sheet

Latin name of genus and species of plant claimed: *Angelonia angustifolia.*
Variety denomination: 'Balangplum'.

BACKGROUND OF THE INVENTION

The present invention relates to a new and distinct cultivar of *Angelonia* plant botanically known as *Angelonia angustifolia* and hereinafter referred to by the cultivar name 'Balangplum'.

The new cultivar was developed by the inventor in a controlled breeding program during October 2001 at Elburn, Ill. The objective of the breeding program was the development of *Angelonia* cultivars with unique flower colors, good basal branching and moderately vigorous growth habit.

The new cultivar was the result of a self-pollination of the proprietary *Angelonia angustifolia* breeding selection designated 175-1, not patented, characterized by its deep purple-colored flowers, medium to light green-colored foliage, tall height, and upright growth habit. The new cultivar was discovered and selected by the inventor as a single flowering plant within the progeny of the above stated self-pollination during April 2002 in a controlled environment at Elburn, Ill.

Asexual reproduction of the new cultivar by terminal stem cuttings since April 2002 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balangplum' as a new and distinct cultivar of *Angelonia* plant:

1. Medium violet-colored flowers;
2. Good basal branching; and
3. Moderately vigorous, upright growth habit.

Plants of the new cultivar differ from plants of the parent primarily in flower color and growth habit.

Of the *Angelonia* cultivars known to the inventor, the most similar to 'Balangplum' is the *Angelonia* cultivar Balangdepi, U.S. Plant Pat. No. 14,656. However, in side-by-side comparisons, plants of the new cultivar differ from plants of 'Balangdepi' in the following characteristics:

1. Plants of the new cultivar have a shorter growth habit compared to 'Balangdepi';
2. Plants of the new cultivar have a narrower plant diameter compared to 'Balangdepi'; and
3. Plants of the new cultivar have smaller flowers, as measured by flower length and width, compared to 'Balangdepi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangplum'. The plants were grown in 10 cm pots for 11 weeks in a greenhouse at West Chicago, Ill.

DETAILED BOTANICAL DESCRIPTION

Figure 1:
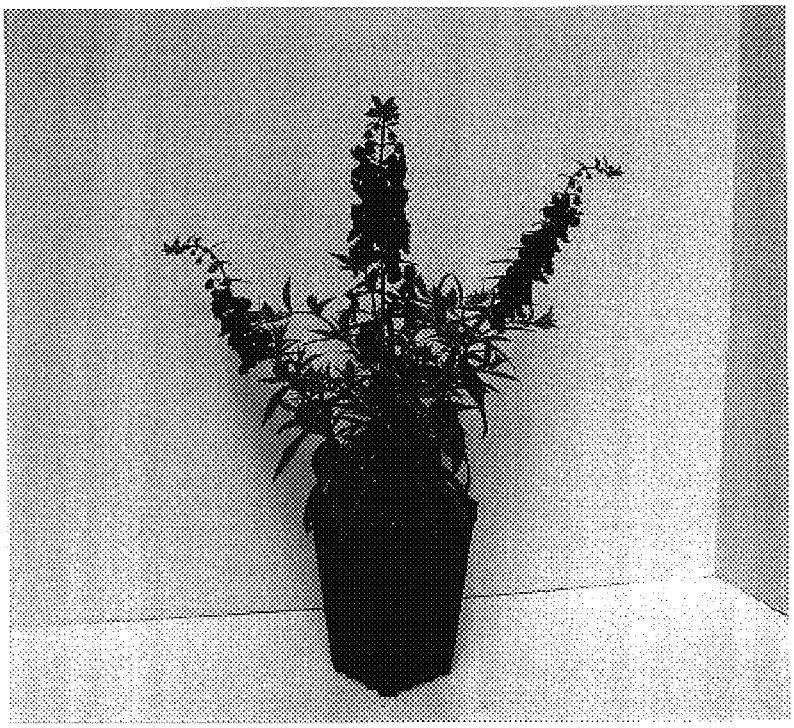
FIG. 1 illustrates a side view of the overall growth and flowering habit of 'Balangplum'.
Figure 2:
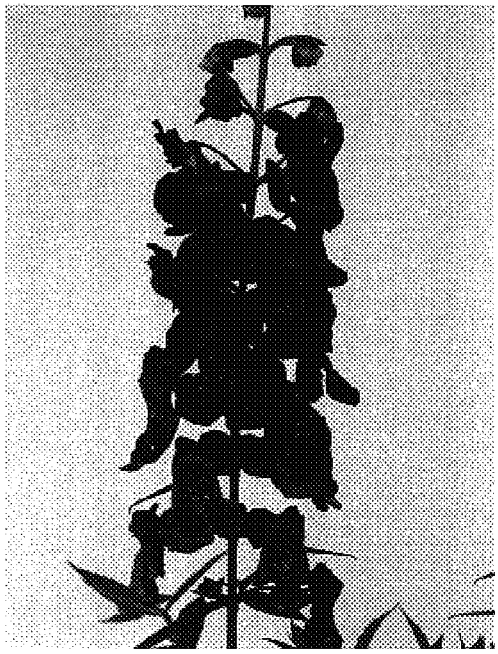
FIG. 2 illustrates a close-up view of the inflorescence of 'Balangplum'.
Figure 3:
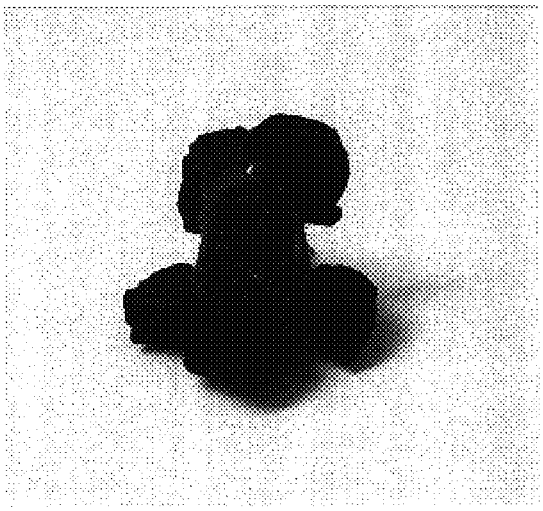
FIG. 3 illustrates a close-up view of an individual flower of 'Balangplum'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Apr. 13, 2005. The readings were taken between 1:00 p.m. and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 11 weeks while utilizing a soilless growth medium. Greenhouse temperatures were maintained at approximately 75° F. to 85° F. (25° C. to 29° C.) during the day and approximately 62° F. to 70° F. (17° C. to 21° C.) during the night. Greenhouse light levels were maintained at approximately 6,000 to 10,000 footcandles during the day.

Botanical classification: *Angelonia angustifolia,* cultivar Balangplum.

Parentage:

*Female (seed) parent.*—Proprietary *Angelonia angustifolia* breeding selection designated 175-1, not patented.

*Male (pollen) parent.*—Proprietary *Angelonia angustifolia* breeding selection 175-1, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous.

*Form.*—Upright.

*Size.*—Height (from soil level to top of plant plane): Approximately 23.7 cm. Diameter (area of spread): Approximately 26.3 cm.

*Main branch.*—Quantity per plant: Approximately 3. Shape: Square in cross section. Strength: Strong. Length from soil level to base of raceme: Approximately 27.8 cm. Diameter: Approximately 3.0 mm. Texture: Densely pubescent with short, straight hairs. Color: Between 145B and 145C. Internode length at middle of branch: Approximately 1.4 cm.

*Foliage.*—Quantity of leaves per main branch: Approximately 19. Type: Simple. Fragrance: None. Arrangement: Opposite. Orientation to stem: Right angle or obtuse. Shape: Elliptic. Margin: Widely dentate. Apex: Acuminate. Base: Sessile. Length of leaf at center of branch: Approximately 5.6 cm. Width of leaf at center of branch: Approximately 1.5 cm. Texture of upper surface: Densely glandular-pubescent. Texture of lower surface: Sparsely glandular-pubescent. Gland color: 145C. Venation pattern: Pinnate. Color of upper surface of young and mature foliage: 139A with venation of 145C. Color of lower surface of young and mature foliage: 137B with venation of 146C.

Flowering description:

*Flowering habit.*—'Balangplum' is freely flowering under outdoor growing conditions with substantially continuous blooming from spring through autumn and year round in greenhouse environment.

*Time to first flower.*—Approximately 12 weeks from sticking of unrooted cutting.

*Lastingness of individual bloom on the plant.*—Approximately 7 to 10 days.

*Inflorescence type/description.*—Terminal racemes. Length: Approximately 9.2 cm. Width: Approximately 4.3 cm. Number per plant: Approximately 2 open racemes per plant at 11 weeks. Number of fully open flowers per raceme at any one time: Approximately 12.

Flower description:

*Type/fragrance.*—Bilabiate. No fragrance.

*Bud.*—Rate of opening: 3 to 4 days from first color to fully open. Shape: Globular. Length: Approximately 8.8 mm. Diameter: Approximately 6.6 mm. Color of upper surface: N82B. Color of lower surface: 86C with spots of N77A.

*Flower size/aspect.*—Length: Approximately 2.1 cm. Width: Approximately 1.7 cm. Depth: Approximately 9.2 mm. Aspect: Facing outward.

*Petals.*—Quantity: Five per flower, fused at base forming a throat, an upper lip having two petals, and a lower lip having three petals— one central petal and one lateral petal on each side. Petal shape of upper lip and lower lip petals: Obovate.

*Upper lip.*—Petal apex: Emarginate. Petal margin: Entire. Length of petals from throat: Approximately 6.0 mm. Width of petals: Approximately 8.3 mm. Color of upper and lower surfaces: First open: Darker than N81A with N87B at base. Fully open: Darker than N81A. Texture of upper surface: Sparsely glandular-pubescent at margin, becoming denser towards base. Texture of lower surface: Glabrous. Gland color: 15D, translucent.

*Lower lip, lateral petals.*—Petal apex: Obtuse. Petal margin: Entire. Length of petals from throat: Approximately 6.9 mm. Width of each petal: Approximately 8.9 mm. Color of upper surface: First open: Slightly darker than N81A. Fully open: N87A. Color of lower surface: First open: N87A. Fully open: N87B. Texture of upper surface: Sparsely glandular-pubescent at margin, becoming denser towards base. Texture of lower surface: Moderately glandular-pubescent. Gland color: 15D, translucent.

*Lower lip, central petal.*—Petal apex: Emarginate. Petal margin: Entire. Length of petal from palate: Approximately 8.2 mm. Width of petal: Approximately 9.6 mm. Color of upper surface: First open: Slightly darker than N81A. Fully open: N87A. Color of lower surface: First open: N81A. Fully open: N87B. Texture of upper surface: Sparsely glandular-pubescent at margin, becoming denser towards base. Texture of lower surface: Moderately glandular-pubescent. Gland color: 15D, translucent.

*Throat.*—Length: Approximately 6.4 mm. Width: Approximately 7.0 mm. Texture of inner and outer surfaces: Glabrous. Color of inner and outer surfaces: Lighter than 77D with spots of N77A. Palate color: First open: 83A. Fully open: 79B. Palate texture: Glabrous. Teeth color: First open: 83A. Fully open: 79B.

*Pedicel.*—Strength: Good. Length: Approximately 1.4 cm. Diameter: Approximately 0.5 mm. Angle to stem: Almost perpendicular to stem. Texture: Densely pubescent. Color: 144A.

*Calyx.*—Shape: Five-pointed star, cupped. Width: Approximately 6.0 mm.

*Sepal.*—Quantity per flower: 5. Shape: Lanceolate. Margin: Entire. Base: Fused. Apex: Acuminate. Length: Approximately 4.2 mm. Width: Approximately 1.7 mm. Texture: Upper or inner surface: Glabrous. Lower or outer surface: Densely glandular-pubescent. Color of upper and lower surfaces: Between 137B and 137C with overlay at base of 186A.

*Reproductive organs.*—Androecium: Stamen quantity: 4 per flower. Stamen length: Approximately 5.0 mm. Filament color: Closest to 155B. Anther shape: Bilobed. Anther length: Approximately 2.0 mm. Anther color: Closest to 86A. Amount of pollen: Abundant. Pollen color: Closest to 4D. Gynoecium: Pistil quantity: 1 per flower. Pistil length: Approximately 4.3 mm. Stigma length: Approximately 0.1 mm. Stigma color: Closest to 155B. Style length: Approximately 3.0 mm. Style color: Closest to 155B. Ovary diameter: Approximately 1.2 mm. Ovary texture: Glabrous. Ovary color: 144C.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangplum', substantially as herein shown and described.

* * * * *